(12) United States Patent
Larson, III et al.

(10) Patent No.: US 7,795,997 B2
(45) Date of Patent: Sep. 14, 2010

(54) APPARATUS AND METHOD FOR MEASURING AN ENVIRONMENTAL CONDITION

(75) Inventors: John D. Larson, III, Palo Alto, CA (US); Storrs T. Hoen, Brisbane, CA (US); Annette C. Grot, Cupertino, CA (US); Richard C. Ruby, Menlo Park, CA (US); Graham M. Flower, San Jose, CA (US)

(73) Assignee: Avago Technologies Wireless IP (Singapore) Pte. Ltd., Singapore (SG)

( * ) Notice: Subject to any disclaimer, the term of this patent is extended or adjusted under 35 U.S.C. 154(b) by 316 days.

(21) Appl. No.: 11/526,948

(22) Filed: Sep. 25, 2006

(65) Prior Publication Data
US 2008/0078233 A1    Apr. 3, 2008

(51) Int. Cl.
*H03H 9/00* (2006.01)

(52) U.S. Cl. .................. 333/187; 310/312

(58) Field of Classification Search ........ 333/187; 310/334, 312; 340/962; 347/56; 73/24.06, 73/24.04, 335.03, 579
See application file for complete search history.

(56) References Cited

U.S. PATENT DOCUMENTS

| | | | | | |
|---|---|---|---|---|---|
| 5,005,015 | A | * | 4/1991 | Dehn et al. | 340/962 |
| 5,587,620 | A | * | 12/1996 | Ruby et al. | 310/346 |
| 6,150,703 | A | * | 11/2000 | Cushman et al. | 257/415 |
| 7,002,281 | B2 | * | 2/2006 | Andle | 310/313 B |
| 7,036,375 | B2 | * | 5/2006 | Nozaki | 73/579 |
| 7,358,651 | B2 | * | 4/2008 | Ruby et al. | 310/334 |
| 7,358,831 | B2 | * | 4/2008 | Larson et al. | 333/187 |
| 7,578,583 | B2 | * | 8/2009 | Chou et al. | 347/56 |
| 2004/0195937 | A1 | * | 10/2004 | Matsubara et al. | 310/320 |
| 2005/0030127 | A1 | * | 2/2005 | Loebl et al. | 333/187 |

* cited by examiner

*Primary Examiner*—Vibol Tan
*Assistant Examiner*—Crystal L Hammond

(57) ABSTRACT

A sensor senses an environmental condition. The sensor includes a film bulk acoustic resonator that includes a layer of material that causes resonant frequency and/or quality factor shifts of the film bulk acoustic resonator in response to changes in the environmental condition. The environmental condition may be relative humidity and the layer of material may be a moisture absorptive material.

26 Claims, 3 Drawing Sheets

US 7,795,997 B2

APPARATUS AND METHOD FOR MEASURING AN ENVIRONMENTAL CONDITION

BACKGROUND OF THE INVENTION

Sensors are known that measure environmental conditions such as temperature, pressure, and relative humidity. For example, thermometers measure temperature and barometers measure pressure. One type of moisture sensor is called a wet/dry bulb thermometer. Typically, such devices includes two thermometers, with one thermometer having its bulb wrapped in a material that is wetted with water. As the water evaporates from the wet thermometer, it absorbs energy from the bulb causing the temperature to drop. By comparing the temperature of the wetted thermometer with that of the normal thermometer, one can determine the relative humidity of the air, with the understanding that more humidity in the air results in a slower evaporation rate and a smaller difference in temperature between the two thermometers.

Other types of relative humidity sensors include moisture sensitive materials that may change color depending upon the moisture level, and capacitors that include water permeable dielectrics. In the latter, the capacitor is part of a circuit, and depending on the humidity, which senses the capacitance changes. This change in capacitance can be related to the relative humidity.

There are a number of problems with the above humidity sensors. For example, the wet/dry bulb thermometer is relatively bulky and, because it has a relatively heavy mass, it takes a significant amount of time to register the changes in temperature that are related to the changes in humidity. The chemical detectors often may only be used once, and may be slower to register a reading as well.

With respect to the capacitor device mentioned above, its use may be limited by its size. More specifically, such devices must have a relatively large capacitor so that changes in the dielectric constant, and thus the capacitance, are large enough to be read by attendant circuitry.

A further problem with all of the humidity sensors mentioned above is that they are not readily useable in remote locations. This is due to the fact that additional circuitry and apparatus is needed to convert their readings into a signal that may be transmitted to a remote receiving station. Similar problems plague other environmental sensors such as temperature and pressure sensors.

SUMMARY OF THE INVENTION

In accordance with one aspect of the present invention, the device provides an electronic sensor that senses an environmental condition. The sensor comprises a film bulk acoustic resonator equipped with a layer of material that causes resonant frequency and/or quality factor shifts of the film bulk acoustic resonator in response to changes in the environmental condition.

The environmental condition may be humidity and the layer of material may comprise a moisture absorptive material. The sensor may further comprise a drive circuit that drives the film bulk acoustic resonator (FBAR) at a known frequency to cause a film bulk acoustic resonator impedance related to the environmental condition. The FBAR may be a series tuned resonant circuit or a parallel tuned resonant circuit. The sensor may further comprise a drive circuit that causes the film bulk acoustic resonator to resonate.

The device circuit may provide a drive output required to cause the film bulk acoustic resonator to resonate. The drive output required to cause the FBAR to resonate is indicative of the film bulk acoustic resonator quality factor and is related to the sensed environmental condition. The FBAR and drive circuit may be configured to form a regenerative oscillator that oscillates at a series or parallel resonant frequency.

The regenerative oscillator may comprise a first regenerative oscillator that oscillates at a first resonant frequency. The sensor may further comprise a second film bulk acoustic resonator and drive circuit configured to form a second regenerative oscillator that oscillates at a second resonant frequency. An enclosure protects the first regenerative oscillator from the environment condition and a different circuit measures differences between the first and second resonant frequencies.

The sensor may further comprise a transmitter. The transmitter may be coupled to the film bulk acoustic resonator and transmit resonant frequency and/or quality factor information related to the sensed environmental condition. According to a further embodiment, a humidity sensor comprises a FBAR. The FBAR has a layer of moisture affected material that causes resonant frequency and/or quality factor shifts of the film bulk acoustic resonator in response to changes in humidity.

According to a further embodiment, a method is provided comprising exposing a film bulk acoustic resonator to an environmental condition, wherein the film bulk acoustic resonator has a layer of material that causes resonant frequency and/or quality factor shifts of the film bulk acoustic resonator in response to changes in the environmental condition. The method further comprises driving the film bulk acoustic resonator with an electrical signal and measuring a condition of the film bulk acoustic resonator.

BRIEF DESCRIPTION OF THE DRAWINGS

The foregoing aspects and many of the attended advantages of this invention will become more readily appreciated as the same become better understood by reference to the following detailed description, when taken in conjunction with the accompanying drawings, wherein.

DESCRIPTION OF THE INVENTION

Figure 1:
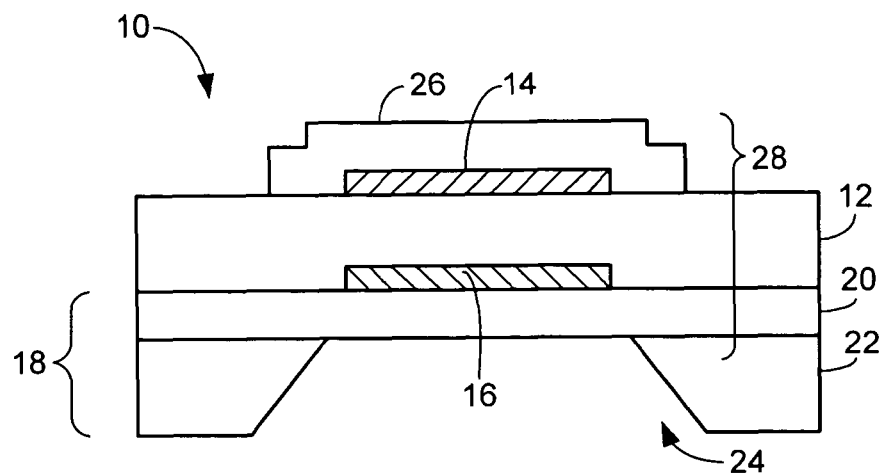
FIG. 1 is a cross-sectional view of a film bulk acoustic resonator according to an embodiment of the present invention.

Referring now to FIG. 1, it shows a film bulk acoustic resonator (FBAR) 10 according to an embodiment of the present invention. The FBAR 10 generally includes a layer 12 of piezoelectric material between a pair of electrodes 14 and 16. The piezoelectric material 12 and electrodes 14 and 16 are formed on a substrate 18 which may comprise a silicon nitride layer 20 deposited over a layer or slice 22 of silicon. As will be noted, a cavity 24 is formed by etching the silicon substrate 22. The piezoelectric material may be, for example, aluminum nitride and the electrodes 14 and 16 may be formed of molybdenum. Lastly, a moisture absorptive material is layered over at least one side of the FBAR 10. The layer 26 of moisture absorptive material, according to this embodiment, is formed over electrode 14 and partly over the piezoelectric material layer 12. The piezoelectric layer 26 may be formed of moisture absorbing materials such as polyimide, sold under the brand name Kapton, or any inorganic material that has a moisture absorption capacity of at least 100 waters. Alternatively, both of the electrodes 14 and 16 may be coated with a thin film of the moisture absorptive material.

FBAR devices are known in the art. For example, descriptions of such devices may be found in U.S. Pat. No. 5,587,620 which issued on Dec. 24, 1996 for tunable FBARs and method for making the same. This patent is owned by the assignee of the present invention and is incorporated herein by reference.

The FBAR 10 of FIG. 1 may be modeled electrically as a series resonant circuit having a capacitor in parallel therewith. More specifically, the series resonant branch of the circuit may have a resistor, an inductor, and a capacitor coupled in series. In parallel with the entire series resonance branch may be a parallel capacitor.

The layers of materials deposited on the silicon slice 22 form an acoustical path 28. According to one embodiment, the FBAR 10 may be approximately 100 microns of a millimeter long and 100 microns wide. The acoustic path 28 may be on the order of, for example, 1 to 2 microns. With these dimensions, the values of the series resistor may be approximately 1 ohm, and the inductor may be approximately 100 nanohenries. The parallel capacitor may be approximately 20 to 100 times greater than the series capacitor. With these dimensions and parameter values, the FBAR 10 would have a first order resonant frequency at approximately 1 to 2 GHz. At the resonant frequencies, the total reactance of the FBAR is approximately 50 ohms. Because the resonant frequencies are in the microwave range, the FBAR may be used to advantage because the total reactants of 50 ohms is compatible with most connections, connecting cables, coaxial cables, or planar transmission lines.

When an electric potential is placed across the electrodes 14 and 16, the piezoelectric aluminum nitride layer 12 will change its shape and basically change its thickness in proportion to the potential. If the signal is a sine wave and placed across the electrodes, the FBAR will oscillate in compression waves between the plates. The thickness of the aluminum nitride layer will oscillate so it will become thinner and thicker as the compression increases and then decreases. With the moisture absorptive material layer 26, both the quality factor (Q) and the resonant frequency of the FBAR will change. More specifically, as the moisture absorptive layer 26 absorbs more moisture, the resonant frequency of the FBAR will decrease along with its Q.

Figure 3:
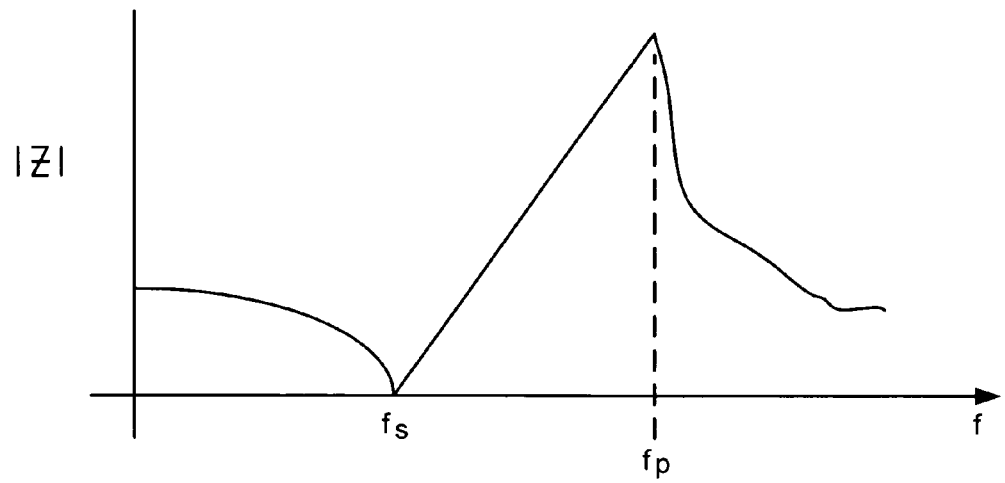
FIG. 3 is a plot illustrating the impedance of the device of FIG. 1 responsive to a series resonant frequency and a parallel resonant frequency.

The FBAR 10 has two resonant modes. This is shown, for example, in FIG. 3. The first resonant mode is at a frequency $f_s$. This resonance mode occurs at the resonant frequency set by the serial inductor and capacitor such that they together appear as 0 ohms so that the total resistance of the FBAR is approximately 1 ohm. The second oscillation mode is a parallel oscillation mode that occurs at frequency $f_p$. This resonant frequency is set by the serial inductor in the summation of the serial capacitor and parallel capacitor. Because capacitors in series have a lower capacitance than either of the capacitors separately, the parallel resonant frequency $f_p$ is higher than the series resonant frequency $f_s$.

Figure 2:
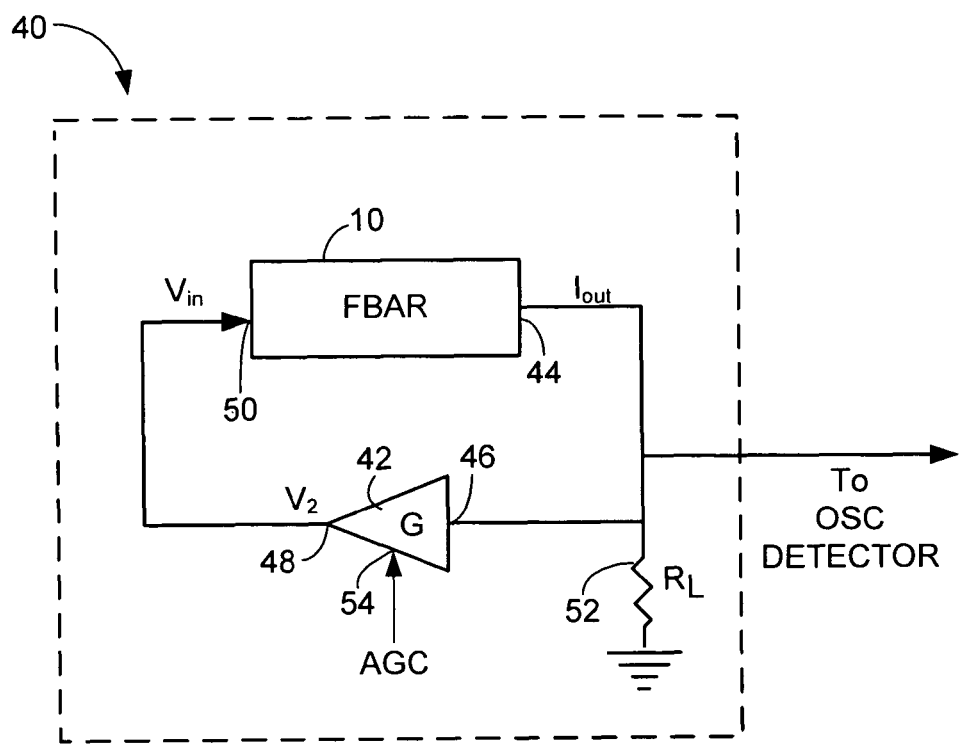
FIG. 2 is a schematic circuit diagram of an environment condition sensor according to one embodiment of the present invention.

FIG. 2 shows a sensor 40 according to an embodiment of the present invention which utilizes the FBAR 10. Here it may be seen that the FBAR 10 is series coupled with a variable gain amplifier 42. The output 44 of the FBAR is coupled to the input 46 of the variable gain amplifier 42. The output 48 of the variable gain amplifier is coupled to the input 50 of the FBAR 10. A resistor 52 is coupled between the output 44 of FBAR 10 and hence the input 46 of amplifier 42 to ground. The voltage across the resistor 52 may be directed as indicated to an oscillation detector.

The amplifier 42 also includes an AGC input 54 for receiving an incrementally increasing AGC voltage. The function of the AGC voltage will be described subsequently. As those skilled in the art will appreciate, the FBAR 10 and the amplifier 42 are configured to form a series regenerative oscillator.

In the sensor 40, the amplifier 42 has a fairly low output impedance. Thus, the FBAR 10 is driven by a fairly low output impedance amplifier. At the series resonant frequency $f_s$, the FBAR exhibits a low impedance (approximately 1 ohm) and thus has a large output current ($I_{out}$) flowing in response to the drive voltage $V_{IN}$ at its input 50. In particular, the output current will be:

$$1)\ I_{OUT} = \frac{V_{IN}}{R_s} = \frac{V_{IN}}{X_o} k_t^2 Q_s$$

where:
$X_o$=capacitive reactance of FBAR
$K_t^2$=electro-acoustic coupling coefficient The current $I_{out}$ flows through the resistor 52 ($R_L$) to appear across the input to the amplifier 42. In turn, an output voltage $V_2$ appears at the output 48 of the amplifier 42. This voltage is equal to $$2)\ V_2 = GV_g = G\frac{V_{IN}}{X_o} k_t^2 Q_s R_L$$

If $V_2$ is equal to $V_{IN}$, then the oscillator circuit will break into oscillation at frequency $f_s$. This occurs when $$3)\ \frac{G_{osc}}{X_o} k_t^2 Q R_L = 1$$

when there is unity loop gain. As may be noted, the gain $G_{osc}$ that causes oscillation will be inversely proportional to the series quality factor ($Q_s$).

To increase the gain G of amplifier 42, a gain control voltage may be applied to the amplifier at input 54. By measuring the control voltage magnitude, one obtains a measure of the series quality factor ($Q_s$). This value of control voltage may be monitored as an indication of the relative humidity.

Figure 4:
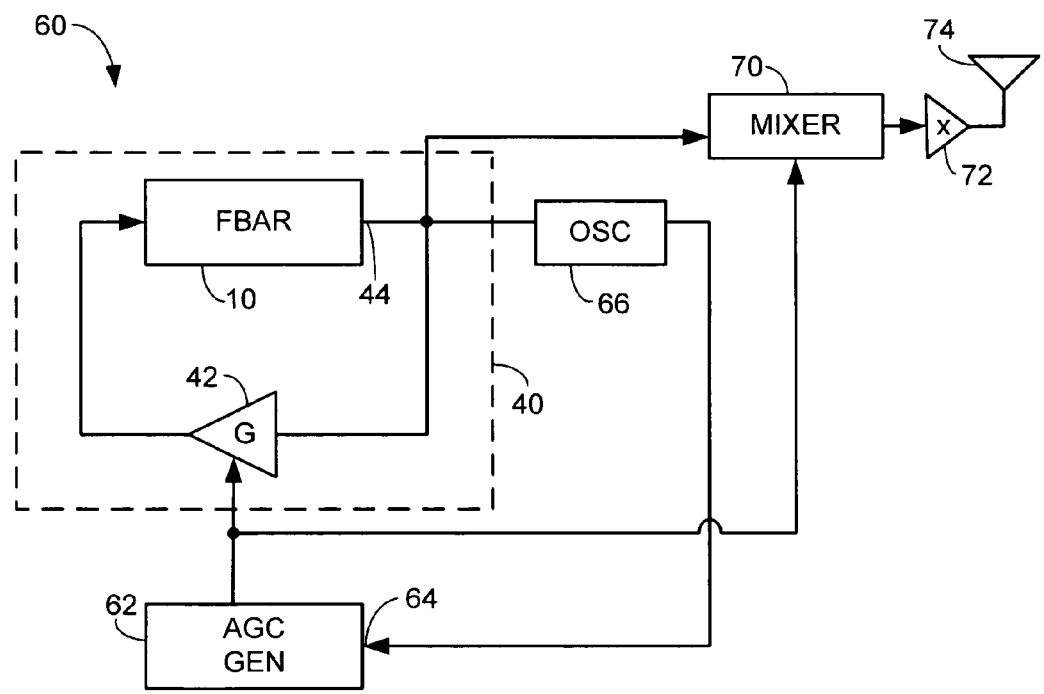
FIG. 4 is a schematic circuit diagram of another environment condition sensor capable of transmitting a signal indicative of the sensed environmental condition according to another embodiment of the present invention.

Referring now to FIG. 4, it shows a further sensor 60 according to another embodiment of the invention. As will be noted, the sensor 60 incorporates the series regenerative oscillator 40 as described with respect to FIG. 2. In FIG. 4 it may be noted that a gain control generator 62 provides a gain control drive voltage to amplifier 42. An oscillation detector 66 is coupled between the output of the FBAR 10 and the input 64 of the gain control generator 62. A mixer 70 mixes the output frequency signal provided at the output 44 of the FBAR 10 and the control voltage generated by the gain control generator 62. The output of the mixer is coupled to a transmitter 72 which then transmits the gain control voltage modulated signal over an antennae 74 to a remote receiver. As a result, the transmitter 72 transmits both the resonant frequency and quality factor information related to the relative humidity sensed by the detector 40. Of course, the signal generated by the mixer 70 and transmitted by the transmitter 72 in the form of the output frequency $f_s$ modulated by the control voltage may alternatively be transmitted over cable as well as a wireless connection.

In the operation of the sensor 60 of FIG. 4, the oscillation detector 66 will cause the gain control voltage generator 62 to ramp its voltage until the series resonant circuit begins to oscillate. The amount of gain needed to maintain oscillation is inversely proportional to the Q of the FBAR. Therefore, the control voltage necessary to cause oscillation is used to modulate the oscillation signal in an amplitude modulation sense by mixer 70. Hence, the Q of the FBAR may be determined by measuring the amplitude of the transmitted signal and the resonant frequency of the FBAR by reading the frequency of the transmitted signal. Here, the smaller the amplitude, the higher the Q.

Figure 5:
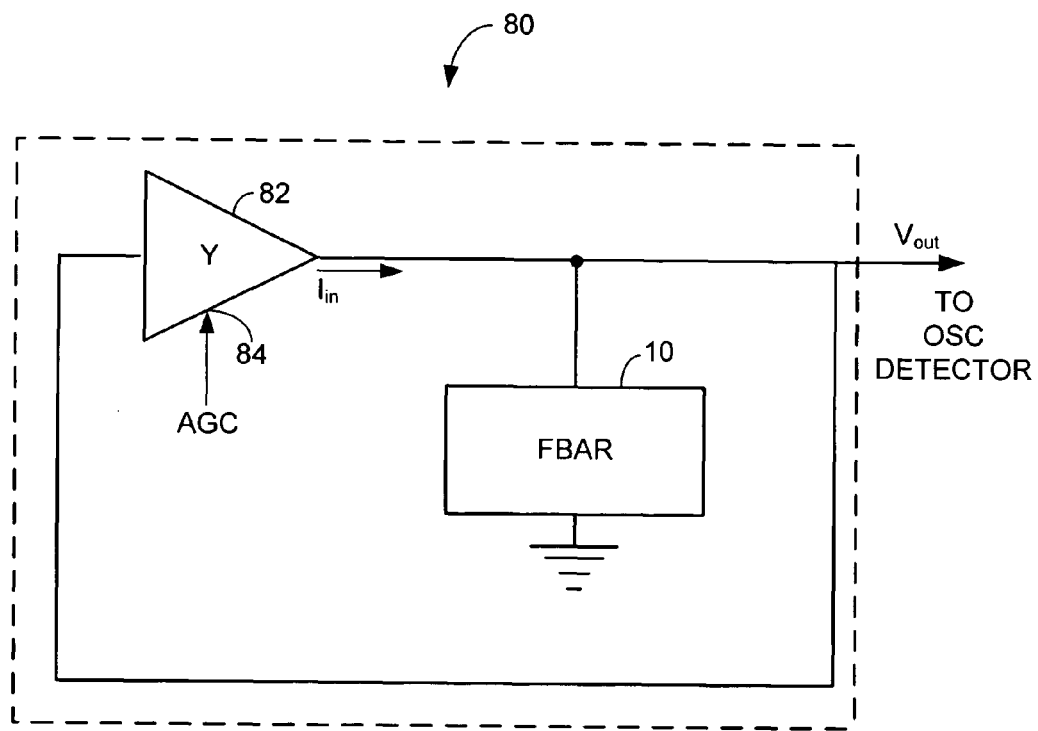
FIG. 5 is a schematic circuit diagram of another environment condition sensor according to a further embodiment of the present invention.

Referring now to FIG. 5, it shows another embodiment of the present invention. The sensor 80 of FIG. 5 includes the FBAR 10 and the variable gain amplifier 82. In this embodiment, the FBAR 10 is driven to its parallel resonance mode as opposed to its series resonance mode. The amplifier 82 has a gain stage Y that has a higher impedance output than the variable gain amplifiers previously described with respect to the series regenerative oscillators. The maximum gain of the circuit would occur when the FBAR has a maximum impedance which occurs at the parallel resonant frequency. This resonant frequency could be monitored by an oscillator detector as indicated.

In one application, the FBAR resonator may be driven with the frequency near its parallel resonant frequency. The impedance of the FBAR may then be measured to obtain a measure of the relative humidity. The separation between the series and parallel resonant frequencies is sufficient to prevent any kind of overlap.

In the parallel circuit configuration of FIG. 5, the output voltage is read across the FBAR 10. $V_{OUT}$ is then equal to $$V_{OUT}=I_{IN}R_p=I_{IN} \cdot k_t^2 Q_p X_o \quad 4)$$

wherein $R_p$ is the FBAR resistance at the parallel resonant frequency and $Q_p$ is the quality factor of the FBAR at the parallel resonant frequency. When the quantity is $$Tk_t^2 Q_p X_o = 1 \quad 5)$$

the circuit will begin to oscillate. The transadmittance gain Y of the amplifier 82 will be ramped until oscillation occurs. The gain control voltage at input 84 that results in the oscillation is then the measure of the Q ($Q_p$).

Hence, the parallel FBAR circuit 80 of FIG. 5 may serve as a sensor that is able to translate an environmental condition variable into a change in FBAR Q. This change in FBAR Q may then be read out as a measure of the environmental condition.

Figure 6:
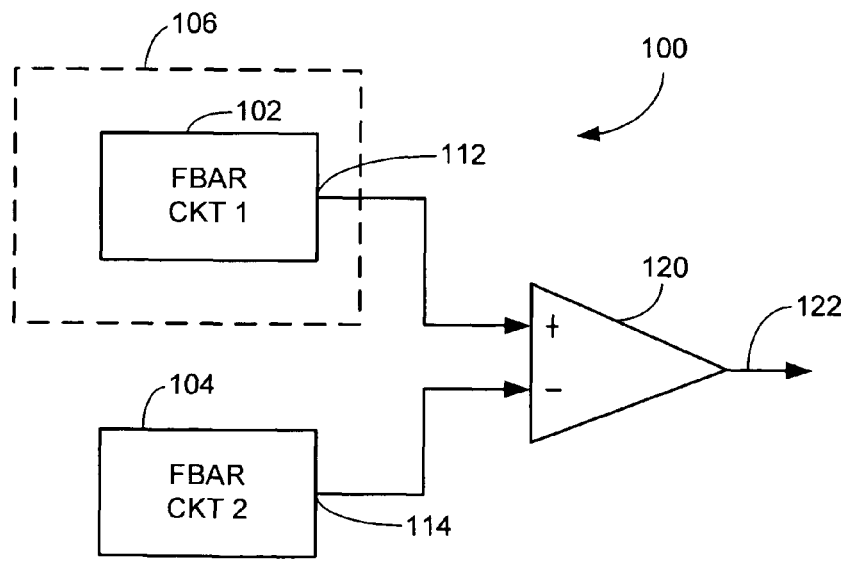
FIG. 6 is a schematic circuit diagram of a further sensor according to a further embodiment of the present invention.

Referring now to FIG. 6, it illustrates a further sensor 100 according to a further embodiment of the invention. The sensor 100 generally includes a first FBAR circuit 102 and a second and identical FBAR circuit 104. The FBAR circuits 102 and 104 may take the form of the series regenerative oscillator of FIG. 2, for example. The first FBAR circuit 102 is confined within a protective enclosure 106 which protects the FBAR circuit 102 from the environmental condition being measured. For example, to measure relative humidity, the FBAR circuit 102 may be placed in a sealed chamber that would isolate the first FBAR circuit 102 from the relative humidity. The first FBAR circuit 102 will be utilized as a reference.

The second FBAR circuit 104 is not so protected from the relative humidity. However, both the FBAR circuit 102 and the FBAR circuit 104 would be exposed to the same atmospheric pressure and temperature. As a result, the difference between the resonant frequencies generated at their outputs 112 and 114, respectively, would be proportional to the relative humidity. The output signals at their respective different resonant frequencies are impressed upon a subtracting circuit 120 which generates a signal at its output 122 representative of the difference between the resonant frequencies of the FBAR circuits 102 and 104.

There are different ways that the various sensor circuits described herein may be calibrated. For example, another sensor may be utilized to characterize the resonant frequency of an FBAR circuit for different humidity points. Circuitry would then read the frequency of the voltage $V_2$ and a lookup table may be utilized to determine the humidity level that the voltage corresponds to.

In another embodiment, an FBAR circuit may be driven with a fixed frequency and its resistance or impedance measured. The measured impedance or resistance would be a gauge of the relative humidity. A lookup table may then be utilized to match the measured impedance with the relative humidity.

There are many advantages to the sensors described herein. First, because the FBAR devices are small and have little mass, they will adapt quickly to the environment in which they are placed quickly. Hence, they will acquire the environment temperature, pressure, or relative humidity quickly as compared to prior art sensors. This increases the speed in which the sensors can provide an accurate read out. Secondly, because the device operates at such a high frequency and such a relatively high Q, relatively small changes in the environmental condition measured (temperature, pressure, or relative humidity) will cause a relative large change in the resonant frequency and in the Q. This serves to amplify these changes so that very small changes in an environmental condition can be read easily and accurately without requiring additional amplification that could produce errors into the result. Further, because the FBAR devices are small, they take very little space. Further still, because the output signal is already a frequency signal, no analog-to-digital converter is needed. All that is required is a counter to count the frequency within a specific time period so as to determine the resonant frequencies. This information would then already be digitized and available for use for accessing a lookup table.

While particular objects and advantages of the present invention have been shown and described in the illustrated embodiments, modifications may be made. It is therefore intended in the appended claims to cover all such changes and modifications which fall within the true spirit and scope of the invention.

We claim:

1. A sensor that senses an environmental condition comprising:
    a film bulk acoustic resonator, comprising: a piezoelectric layer: and a layer of material that causes a change in a resonant frequency and in a quality factor (Q) of the film bulk acoustic resonator in response to changes in the environmental condition.

2. The sensor of claim 1, wherein the environmental condition is humidity and wherein the layer of material comprises a moisture absorptive material.

3. The sensor of claim 1, further comprising a drive circuit that drives the film bulk acoustic resonator at a known frequency to cause a film bulk acoustic resonator impedance related to the environmental condition.

4. The sensor of claim 1, wherein the film bulk acoustic resonator is a series tuned resonant circuit.

5. The sensor of claim 1, wherein the film bulk acoustic resonator is a parallel tuned resonant circuit.

6. The sensor of claim 1, further comprising a drive circuit that causes the film bulk acoustic resonator to resonate.

7. The sensor of claim 6, wherein the drive circuit provides a drive output required to cause the film bulk acoustic resonator to resonate and wherein the drive output required to cause the film bulk acoustic resonator to resonate is indicative of the film bulk acoustic resonator quality factor and is related to the sensed environmental condition.

8. The sensor of claim 6, wherein the film bulk acoustic resonator and drive circuit are configured to form a regenerative oscillator that oscillates at a resonant frequency.

9. The sensor of claim 8, wherein the regenerative oscillator comprises a first regenerative oscillator that oscillates at a first resonant frequency, wherein the sensor further comprises a second film bulk acoustic resonator and drive circuit configured to form a second regenerative oscillator that oscillates at a second resonant frequency, an enclosure protecting the first regenerative oscillator from the environmental condition, and a difference circuit that measures differences between the first and second resonant frequencies.

10. The sensor of claim 1, further comprising a transmitter coupled to the film bulk acoustic resonator that transmits resonate frequency and/or quality factor information related to the sensed environmental condition.

11. A humidity sensor comprising:
a film bulk acoustic resonator, comprising a piezoelectric layer: and a layer of moisture affected material that causes a change in a resonant frequency and in a quality factor (Q) of the film bulk acoustic resonator in response to changes in humidity.

12. The sensor of claim 11, wherein the environmental condition is humidity and wherein the moisture absorptive material is an inorganic material that has an absorption capacity of at least one-hundred waters.

13. The sensor of claim 11, further comprising a drive circuit that drives the film bulk acoustic resonator at a known frequency to cause a film bulk acoustic resonator impedance related to the humidity.

14. The sensor of claim 11 wherein the film bulk acoustic resonator is a series tuned resonant circuit.

15. The sensor of claim 11, wherein the film bulk acoustic resonator is a parallel tuned resonant circuit.

16. The sensor of claim 11, further comprising a drive circuit that causes the film bulk acoustic resonator to resonate.

17. The sensor of claim 16, wherein the film bulk acoustic resonator and drive circuit are configured to form a regenerative oscillator that oscillates at a resonant frequency.

18. The sensor of claim 17, wherein the regenerative oscillator comprises a first regenerative oscillator that oscillates at a first resonant frequency, wherein the sensor further comprises a second film bulk acoustic resonator and drive circuit configured to form a second regenerative oscillator that oscillates at a second resonant frequency, an enclosure protecting the first regenerative oscillator from the environmental condition, and a difference circuit that measures differences between the first and second resonant frequencies.

19. The sensor of claim 16, wherein the drive circuit provides a drive output required to cause the film bulk acoustic resonator to resonate and wherein the drive output required to cause the film bulk acoustic resonator to resonate is indicative of the film bulk acoustic resonator quality factor and is related to sensed humidity level.

20. The sensor of claim 11, further comprising a transmitter coupled to the film bulk acoustic resonator that transmits resonate frequency and/or quality factor information related to the sensed humidity.

21. A method comprising:
exposing a film bulk acoustic resonator to an environmental condition, the film bulk acoustic resonator comprising a piezoelectric layer, and a layer of material that causes a change in a resonant frequency and in a quality factor of the film bulk acoustic resonator in response to changes in the environmental condition;
driving the film bulk acoustic resonator with an electrical signal; and
measuring a condition of the film bulk acoustic resonator.

22. The method of claim 21, wherein the measuring step includes measuring the quality factor of the film bulk acoustic resonator.

23. The method of claim 21, wherein the driving step includes driving the film bulk acoustic resonator with an increasing signal amplitude until the film bulk acoustic resonator to resonate and wherein the measuring step includes measuring the amplitude of the electrical signal.

24. The method of claim 21, wherein the measuring step includes measuring impedance of the film bulk acoustic resonator.

25. The method of claim 21, wherein the environmental condition is humidity.

26. The method of claim 21, wherein the measuring step provides a measurement of the environmental condition, and wherein the method further comprises transmitting the method.

* * * * *